United States Patent
Guerra et al.

(10) Patent No.: US 12,122,929 B2
(45) Date of Patent: Oct. 22, 2024

(54) COPOLYMERS OF PERFLUOROCYCLOALIPHATIC METHYL VINYL ETHER

(71) Applicant: 3M INNOVATIVE PROPERTIES COMPANY, St. Paul, MN (US)

(72) Inventors: Miguel A. Guerra, Woodbury, MN (US); Tatsuo Fukushi, Woodbury, MN (US); Bradford L. Ryland, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 769 days.

(21) Appl. No.: 17/289,319

(22) PCT Filed: Nov. 13, 2019

(86) PCT No.: PCT/US2019/061066
§ 371 (c)(1),
(2) Date: Apr. 28, 2021

(87) PCT Pub. No.: WO2020/102271
PCT Pub. Date: May 22, 2020

(65) Prior Publication Data
US 2022/0033673 A1    Feb. 3, 2022

Related U.S. Application Data

(60) Provisional application No. 62/767,054, filed on Nov. 14, 2018.

(51) Int. Cl.
*C09D 129/10* (2006.01)
*C07C 21/18* (2006.01)
(Continued)

(52) U.S. Cl.
CPC ............ *C09D 129/10* (2013.01); *C07C 21/18* (2013.01); *C08F 216/1408* (2013.01); *C08F 2800/10* (2013.01)

(58) Field of Classification Search
CPC .... C09D 129/10; C09D 127/18; C07C 21/18; C08F 216/1408; C08F 2800/10; C08F 214/262
See application file for complete search history.

(56) References Cited

U.S. PATENT DOCUMENTS 2,567,011 A    9/1951    Diesslin
2,732,398 A    1/1956    Brice
(Continued)

FOREIGN PATENT DOCUMENTS

CA    2522837    6/2000
JP    2001-354720 A    12/2001
(Continued)

OTHER PUBLICATIONS

Machine translation of JP 2006-16540. (Year: 2006).*
(Continued)

*Primary Examiner* — Catherine S Branch
(74) *Attorney, Agent, or Firm* — Julie Lapos-Kuchar

(57) ABSTRACT

Described herein is a perfluoropolymer and compositions therefrom. The perfluoropolymer is derived from: (a) no more than 88 mol % tetrafluoroethylene monomer; and (b) a complementary amount of a perfluoro (cycloaliphatic methyl vinyl ether) monomer, and has substantially no melting point.

19 Claims, 2 Drawing Sheets

(51) Int. Cl.
  *C08F 214/26* (2006.01)
  *C08F 216/14* (2006.01)
  *C09D 127/18* (2006.01)

(56) References Cited

U.S. PATENT DOCUMENTS

| | | | |
|---|---|---|---|
| 4,138,426 A | 2/1979 | England |
| 4,275,226 A | 6/1981 | Yamabe |
| 4,530,569 A | 7/1985 | Squire |
| 4,897,457 A | 1/1990 | Nakamura |
| 5,051,114 A | 9/1991 | Nemser |
| 5,268,405 A | 12/1993 | Ojakaar |
| 5,426,165 A | 6/1995 | Kruger |
| 5,545,693 A | 8/1996 | Hung |
| 6,479,161 B1 | 11/2002 | Araki |
| 6,833,403 B1 | 12/2004 | Blaedel |
| 7,351,471 B2 | 4/2008 | Jing |
| 7,381,774 B2 | 6/2008 | Bish |
| 7,537,828 B2 | 5/2009 | Coggio |
| 7,671,112 B2 | 3/2010 | Hintzer |
| 8,013,064 B2 | 9/2011 | Nakazato |
| 9,023,977 B2 | 5/2015 | Corveleyn |
| 9,290,619 B2 | 3/2016 | Guerra |
| 9,803,039 B2 | 10/2017 | Corveleyn |
| 9,862,852 B2 | 1/2018 | Mugisawa |
| 9,902,836 B2 | 2/2018 | Corveleyn |
| 2001/0051753 A1 | 12/2001 | Navarrini |
| 2003/0088040 A1 | 5/2003 | Arrigoni et al. |
| 2004/0236028 A1 | 11/2004 | Hung |
| 2006/0147177 A1 | 7/2006 | Jing |
| 2007/0093625 A1 | 4/2007 | Arrogoni et al. |
| 2012/0009438 A1 | 1/2012 | Dams |
| 2013/0261249 A1 | 10/2013 | Apostolo et al. |
| 2014/0066572 A1 | 3/2014 | Corveleyn |
| 2015/0259558 A1 | 9/2015 | Mugisawa |
| 2017/0044367 A1 | 2/2017 | Corveleyn |

FOREIGN PATENT DOCUMENTS

| | | |
|---|---|---|
| JP | 2003-160616 A | 6/2003 |
| JP | 2006-016540 | 1/2006 |
| JP | 2018-087341 A | 6/2018 |
| WO | WO 1995-002634 | 1/1995 |
| WO | WO 2002-004534 | 1/2002 |
| WO | 2004-0506491 A1 | 6/2004 |

OTHER PUBLICATIONS

Friesen, "Outstanding telechelic perfluoropolyalkylethers and applications therefrom," Progress in Polymer Science, 2018, vol. 81, pp. 238-280.

Funaki, "Tetrafluoroethylene copolymers having good impermeability against gases and chemicals", Database CA [Online] Chemical Abstracts Service, Columbus, Ohio, US, XP002796848, retrieved from STN Database accession No. 2006: 51185, 2 pages.

Yuminov, "Polyfluoroalkyl Polyfluorovinyl Ethers. II .* Synthesis of Perfluoro(cyclohexylmethyl) Perfluorovinyl Ether", Russian Journal of Organic Chemistry, 1995, vol. 31, No. 8, pp. 1040-1043.

International Search Report for PCT International Application No. PCT/IB2019/061066, mailed on Jul. 20, 2020, 6 pages.

* cited by examiner

COPOLYMERS OF PERFLUOROCYCLOALIPHATIC METHYL VINYL ETHER

TECHNICAL FIELD

Amorphous copolymers of tetrafluoroethylene and perfluoro(cycloaliphatic methyl vinyl ether) are described, along with compositions thereof.

SUMMARY

Perfluorinated polymers are known for their outstanding chemical, thermal and surface properties. Perfluorinated polymers such as PTFE (polytetrafluoroethylene), FEP (copolymer of tetrafluoropropylene and hexafluoroethylene), and PFA (copolymer of tetrafluoroethylene and perfluoroether monomers) are crystalline materials which generally suffer from poor optical clarity and poor solubility.

Amorphous perfluoropolymers have been proposed. For example, U.S. Pat. No. 4,530,569 (Squire) describes a copolymer of TFE (tetrafluoroethylene) with perfluoro-2,2-dimethyl-1,3-dioxole (PDD). However, the PDD monomer is expensive and the polymerization is a solution polymerization.

The present disclosure is directed toward an amorphous fluoropolymer, which is able to be polymerized via an emulsion polymerization and/or is less expensive to make.

In one aspect, a perfluoropolymer is described, wherein the perfluoropolymer is derived from: no more than 88 mol % tetrafluoroethylene monomer; and a complementary amount of a monomer according to Formula I, $$Rf-CF_2-[OCF(CF_3)CF_2]_nO-CF=CF_2 \quad (I)$$

wherein $R_f$ is a perfluorinated group comprising 6 carbon atoms and 11 fluorine atoms and a cycloaliphatic group and n is 0, 1, or 2, and wherein the perfluoropolymer has substantially no melting point.

In another aspect, a fluoropolymer is described, the fluoropolymer comprising at least one interpolymerized monomeric unit of

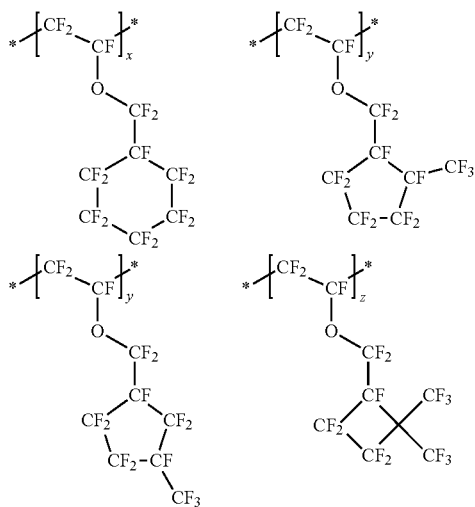

and combinations thereof.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term

Figure 1:
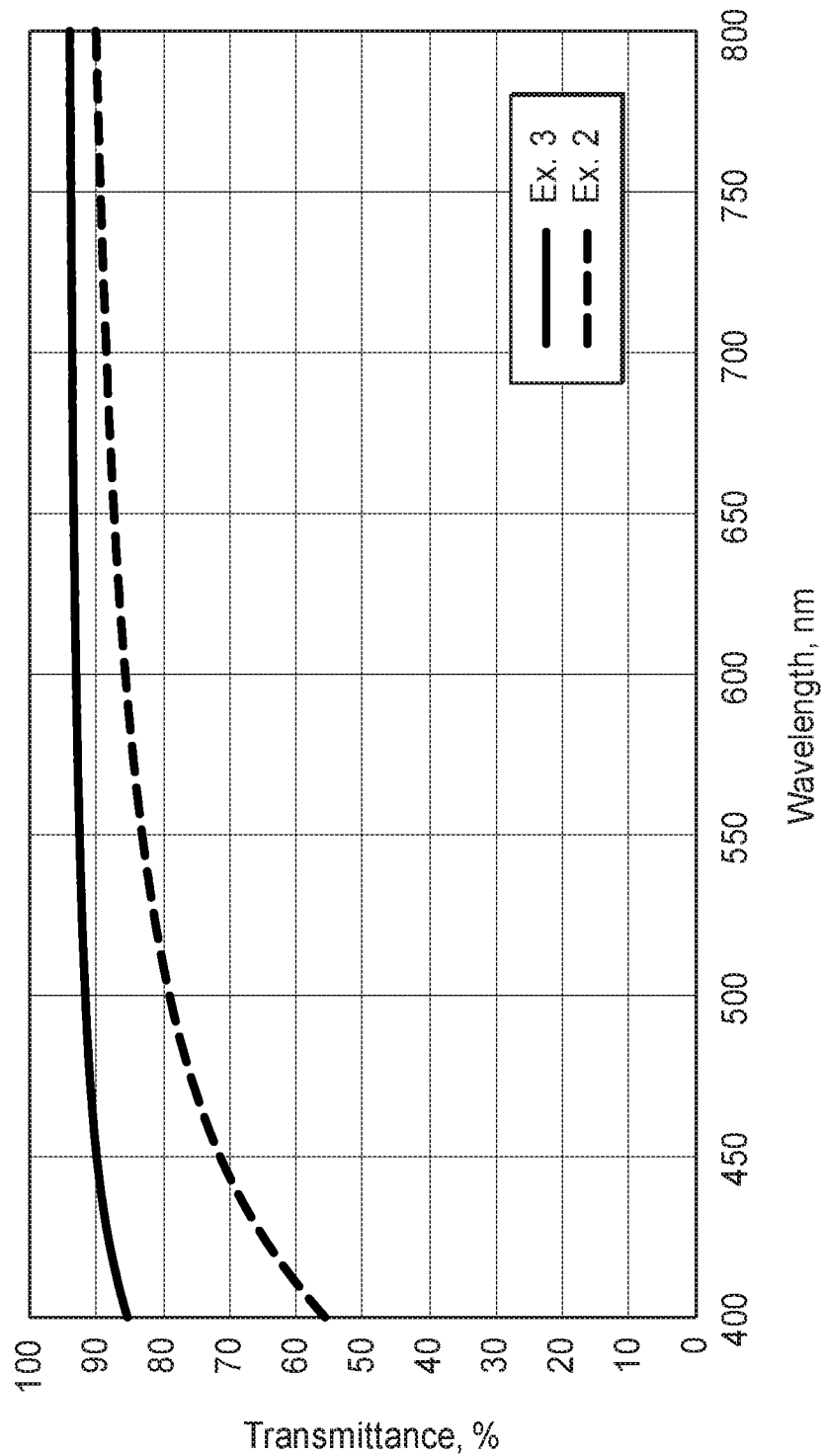
FIG. 1 is the percent specular transmittance versus wavelength for Examples 2 and 3.

"a", "an", and "the" are used interchangeably and mean one or more; and

"and/or" is used to indicate one or both stated cases may occur, for example A and/or B includes, (A and B) and (A or B);

"backbone" refers to the main continuous chain of the polymer, excluding the sites of polymer initiation and termination;

"copolymer" hereafter refers to the polymerization of at least two different monomer and can include tripolymers (three different monomers), tetrapolymers (four different monomers), etc.;

"crosslinking" refers to connecting two pre-formed polymer chains using chemical bonds or chemical groups;

"complementary" means that the mole percentage of perfluoro(cycloaliphatic methyl vinyl ether) monomer plus the mole percentages of TFE and any other monomers present in the copolymer add together to 100%;

"cure site" refers to functional groups, which may participate in crosslinking;

"interpolymerized" refers to monomers that are polymerized together to form a polymer backbone;

"monomer" is a molecule which can undergo polymerization which then form part of the essential structure of a polymer;

"perfluorinated" means a group, a compound, or a molecule derived from a hydrocarbon wherein all hydrogen atoms have been replaced by fluorine atoms. A perfluorinated compound may however still contain other atoms than fluorine and carbon atoms, like oxygen atoms, chlorine atoms, bromine atoms and iodine atoms; and "polymer" refers to a macrostructure having a number average molecular weight (Mn) of at least 50,000 dalton, at least 100,000 dalton, at least 300,000 dalton, at least 500,000 dalton, at least, 750,000 dalton, at least 1,000,000 dalton, or even at least 1,500,000 dalton and not such a high molecular weight as to cause premature gelling of the polymer.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

As used herein, "comprising at least one of" A, B, and C refers to element A by itself, element B by itself, element C by itself, A and B, A and C, B and C, and a combination of all three.

The present disclosure relates to a perfluoropolymer derived from tetrafluoroethylene (TFE) and perfluoro(cycloaliphatic methyl vinyl ether). The polymer disclosed herein is perfluorinated, meaning that polymer comprises C—F bonds and no C—H bonds, however, the polymer may have some C—H bonds at the terminal ends of the polymer, where the polymerization is initiated or terminated. The perfluoropolymer is amorphous, having no detectable melting point by differential scanning calorimetry (DSC). If studied under DSC, the polymer would have no melting point or melt transitions with an enthalpy more than 2 milliJoules/g by DSC.

The perfluoropolymer is derived from no more than 90, 88, 85, 80, 75, 70, 60, or even 50 mol % of TFE. In one embodiment, the perfluoropolymer is derived from at least 10, 20, 30, 40, 50, 60, or even 65 mol % TFE based on the total moles on monomers in the perfluoropolymer.

The perfluoro(cycloaliphatic methyl vinyl ether) is a monomer according to Formula I: $Rf-CF_2-[OCF(CF_3)CF_2]_nO-CF=CF_2$ (I) wherein $R_f$ is a perfluorinated group comprising 6 carbon atoms and 11 fluorine atoms and a cycloaliphatic group and n is 0, 1, or 2. Exemplary $R_f$ groups include: perfluorocyclohexyl, perfluoro(methyl cyclopentyl), and perfluoro(dimethyl cyclobutyl) groups. The perfluoro(cycloaliphatic methyl vinyl ether) monomer can be synthesized using techniques known in the art, for example, by fluorination (e.g., by electrochemical fluorination or direct fluorination) of methyl benzoate, followed by isolation of the perfluorocyclohexyl acid fluoride, which is then reacted with hexafluoropropylene oxide (HFPO) and a catalytic amount of potassium fluoride in an aprotic solvent, followed by decarboxylation of the HFPO coupled adduct(s) to isolate the 1:1 coupled adduct, perfluorocyclohexyl methyl vinyl ether, the 2:1 coupled adduct, perfluorocyclohexyl methoxypropoxy vinyl ether, and higher coupled adducts.

Depending on how the perfluoro(cycloaliphatic methyl vinyl ether) was synthesized and/or whether or not it was purified, the perfluoro(cycloaliphatic methyl vinyl ether) may be a mixture of isomers such as perfluoro(cyclohexyl methyl vinyl ether), perfluoro(2-methyl cyclopentyl methyl vinyl ether), perfluoro(3-methyl cyclopentyl methyl vinyl ether), perfluoro(2-dimethyl cyclobutyl methyl vinyl ether), and/or perfluoro(3-dimethyl cyclobutyl methyl vinyl ether), or one particular isomer such as perfluoro(cyclohexyl methyl vinyl ether). Similar isomers for the Rf group may be seen for the 2:1 coupled adduct.

The perfluoropolymer is derived from a complementary amount of perfluoro(cycloaliphatic methyl vinyl ether) according to Formula I. For example, at least 0.2, 0.4, 0.5, 1, 5, 10, 15, 20, 25, 30, 35, 40, 45, or even 50 mol % of the perfluoro(cycloaliphatic methyl vinyl ether) based on the total moles on monomers in the perfluoropolymer. In one embodiment, at most 1, 2, 5, 10, 15, 20, 25, 30, 35, 40, 45, or even 50 mol % of the perfluoro(cycloaliphatic methyl vinyl ether) is used based on the total moles on monomers in the perfluoropolymer.

The perfluoropolymer disclosed herein may be derived from other perfluorinated monomers as known in the art. Exemplary other perfluorinated monomers include: hexafluoropropylene (HFP), trifluorochloroethylene (CTFE), perfluorovinyl ethers (including perfluoroalkyl vinyl ethers and perfluoroalkoxy vinyl ethers), perfluoroallyl ethers (including perfluoroalkyl allyl ethers and perfluoroalkoxy allyl ethers), perfluorobis-olefins, perfluoro-2,2-dimethyl-1,3-dioxole (PDD), perfluorodimethylene-bis(perfluorovinyl ether), and combinations thereof.

Suitable perfluoroalkyl vinyl monomers correspond to the general formula: $CF_2=CF-R^d_f$ wherein $R^d_f$ represents a perfluoroalkyl group of 1-10, or even 1-5 carbon atoms.

Examples of perfluorovinyl ethers that can be used in the present disclosure include those that correspond to the formula: $CF_2=CF-O-R_f$ wherein $R_f$ represents a perfluorinated aliphatic group that may contain no, one, or more than one oxygen atoms and up to 12, 10, 8, 6 or even 4 carbon atoms. Exemplary perfluorinated vinyl ethers correspond to the formula: $CF_2=CFO(R^a_fO)_n (R^b_fO)_m R^c_f$ wherein $R^a_f$ and $R^b_f$ are different linear or branched perfluoroalkylene groups containing 1-6 carbon atoms, in particular 2-6 carbon atoms, m and n are independently 0-10 and $R^c_f$ is a perfluoroalkyl group containing 1-6 carbon atoms. Specific examples of perfluorinated vinyl ethers include: perfluoro (methyl vinyl) ether (PMVE), perfluoro (ethyl vinyl) ether (PEVE), perfluoro (n-propyl vinyl) ether (PPVE-1), perfluoro-2-propoxypropylvinyl ether (PPVE-2), perfluoro-3-methoxy-n-propylvinyl ether, perfluoro-2-methoxy-ethylvinyl ether, $CF_3-(CF_2)_2-O-CF(CF_3)-CF_2-O-CF(CF_3)-CF_2-O-CF=CF_2$, and perfluoro-methoxy-methylvinylether ($CF_3-O-CF_2-O-CF=CF_2$), and mixtures thereof.

Examples of perfluoroallyl ethers that can be used in the present disclosure include those that correspond to the formula: $CF_2=CF(CF_2)-O-R_f$ wherein $R_f$ represents a perfluorinated aliphatic group that may contain no, one, or more than one oxygen atoms and up to 10, 8, 6 or even 4 carbon atoms. Specific examples of perfluorinated allyl ethers include: $CF_2=CF_2-CF_2-O-(CF_2)_nF$
  wherein n is an integer from 1 to 5, and
  $CF_2=CF_2-CF_2-O-(CF_2)_x-O-(CF_2)_y-F$ wherein x is an integer from 2 to 5 and y is an integer from 1 to 5. Specific examples of perfluorinated allyl ethers include: perfluoro (methyl allyl) ether ($CF_2=CF-CF_2-O-CF_3$), perfluoro (ethyl allyl) ether, perfluoro (n-propyl allyl) ether, perfluoro-2-propoxypropyl allyl ether, perfluoro-3-methoxy-n-propylallyl ether, perfluoro-2-methoxy-ethyl allyl ether, perfluoro-methoxy-methyl allyl ether, and $CF_3-(CF_2)_2-O-CF(CF_3)-CF_2-O-CF(CF_3)-CF_2-O-CF_2CF=CF_2$, and mixtures thereof.

Examples of perfluorobis-olefins that can be used in the present disclosure include those that correspond to the formula $R^1_f R^2_f C=CR^3_f-Z-CR^4_f=CR^5_f R^6_f$ where $R^1_f$, $R^2_f$, $R^3_f$, $R^4_f$, and $R^5_f$ are independently selected from F, or a perfluoroalkyl group containing 1 to 18 carbon atoms and Z is a perfluorinated alkylene or cycloalkylene radical, which is linear or branched. Specific examples of perfluorinated bis-olefin monomers include: $CF_2=CF-C_4F_8-CF=CF_2$, $CF_2=CF-C_2F_4-CF=CF_2$, and $CF_2=CF-C_6F_{12}-CF=CF_2$.

In one embodiment, the perfluoropolymer is derived from at least 0.5, 1, 5, 10, 15, 20, 25, 30, 40, or even 50 mol % of these other perfluorinated monomers. In one embodiment, the perfluoropolymer is derived from at most 5, 10, 15, 20, 25, 30, 40, or even 50 mol % of these other perfluorinated monomers.

In one embodiment, the perfluoropolymer may be synthesized such that the perfluoropolymer comprises groups which aid adhesion to substrate. Such groups can include silanes, phosphates, or especially when adhering to metal substrates, acidic groups such as carboxylic acid groups. Typically, at least 0.5, 0.75, or even 1 moles of groups per moles per moles of monomer used to make the fluorinated polymer are needed. In one embodiment, at most 2, 3, 4, or even 5 moles of groups per moles per moles of monomer used to make the fluorinated polymer are needed.

In one embodiment, the perfluoropolymer disclosed is not derived from PDD.

In one embodiment, the perfluoropolymer disclosed herein is substantially free (i.e., comprises less than 5, 2, 1, or even 0.5 mol % or none) of cyclic groups located along the polymer backbone such as those disclosed in U.S. Pat. No. 4,897,457 (Nakamura et al.).

In one embodiment, the perfluoropolymer is derived from a perfluorinated vinyl ether monomer comprising at least one reactive group, wherein the reactive group is selected from an acid and/or an ester. An exemplary perfluorinated vinyl ether monomer is of the formula $CF_2=CF-O-[CF_2-CF(CF_3)O]_n(C_mF_{2m})-Y$, wherein Y is COOH, COOM, COOR, $SO_2F$, $SO_3H$, $SO_3M$, $P(O)(OH)_2$, where M is a cationic metal (e.g., alkali), which is charge balanced with the anionic group, and R is an alkyl group comprising 1 to 6 carbon atoms. The presence of these reactive groups on the perfluoropolymer can enable improved bonding of the perfluoropolymer of the present disclosure to substrates. Exemplary perfluorinated vinyl ether acids and perfluorinated vinyl ether esters include $CF_2=CF-O-[CF_2-CF(CF_3)O-]_n-(C_mF_{2m})-C(=O)OH$ and $CF_2=CF-O-[CF_2-CF(CF_3)O]_n-(C_mF_{2m})-C(=O)OR$ where n is 0 or 1 and m is an integer from 3 to 12 and R is an alkyl group comprising 1 to 6 carbon atoms. In one embodiment, the $(C_mF_{2m})$ group is linear. In another embodiment, the $(C_mF_{2m})$ group is branched. In one embodiment R is $-CF_3$. Synthesis of such compounds are disclosed in U.S. Pat. No. 4,275,226 (Yamabe et al.), U.S. Pat. No. 4,138,426 (England), and U.S. Pat. No. 6,479,161 (Araki). Exemplary compounds include: $CF_2=CF-O-C_5F_{10}COOH$, $CF_2=CF-O-C_5F_{10}COONa$, $CF_2=CF-O-C_5F_{10}COOCH_3$, $CF_2=CF-O-C_4F_8SO_2F$, $CF_2=CF-O-C_4F_8SO_3H$, $CF_2=CF-O-C_4F_8SO_3K$, $CF_2=CF-O-C_4F_8P(O)(OH)_2$.

In one embodiment, the perfluoropolymer disclosed herein comprises at least one interpolymerized monomeric unit selected from at least one of

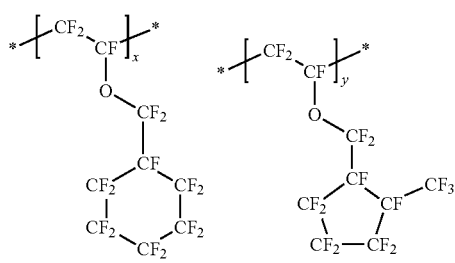

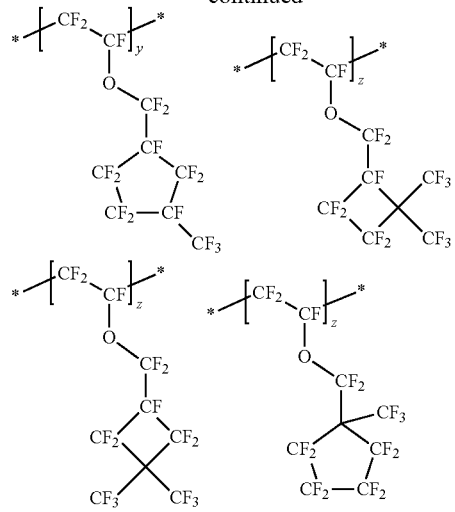

and combinations thereof.

where * denotes the interpolymerized unit is connected to other atoms in the polymer backbone and x, y, and z are the number of times the monomer unit appears (randomly) along the polymer backbone. In one embodiment, x, y, and z are independently at least 2, 5, 7, 10, or even 12 repeat units. Additional repeat units derived from TFE and optionally, from the other perfluorinated monomers, are present along the perfluoropolymer backbone. In one embodiment of the present disclosure, the interpolymerized unit

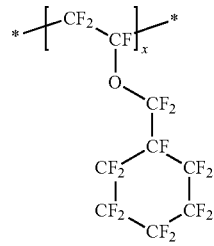

is repeated at least 2, 5, 7, 10, or even 12 times randomly along the polymer backbone.

The perfluoropolymers of the present disclosure can be obtained with any of the known polymerization techniques, however, the fluoropolymers are preferably made through an aqueous emulsion polymerization process, which can be conducted in a known manner including batch, semi-batch, or continuous polymerization techniques. The reactor vessel for use in the aqueous emulsion polymerization process is typically a pressurizable vessel capable of withstanding the internal pressures during the polymerization reaction. Typically, the reaction vessel will include a mechanical agitator, which will produce thorough mixing of the reactor contents and heat exchange system. Any quantity of the monomer(s) may be charged to the reactor vessel. The monomers may be charged batchwise or in a continuous or semi-continuous manner. By semi-continuous it is meant that a plurality of batches of the monomer are charged to the vessel during the course of the polymerization. The independent rate at which the monomers are added to the kettle will depend on the consumption rate of the particular monomer with time. Preferably, the rate of addition of monomer will equal the rate of consumption of monomer, i.e. conversion of monomer into polymer.

The reaction kettle is charged with water, the amounts of which are not critical. To the aqueous phase there is generally also added a fluorinated surfactant, typically a non-telogenic fluorinated surfactant, although aqueous emulsion polymerization without the addition of fluorinated surfactant may also be practiced. When used, the fluorinated surfactant is typically used in amount of 0.01% by weight to 1% by weight. Suitable fluorinated surfactants include any fluorinated surfactant commonly employed in aqueous emulsion polymerization. In one embodiment, the fluorinated surfactants are of the general formula:

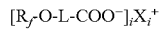

wherein L represents a linear partially or fully fluorinated alkylene group or an aliphatic hydrocarbon group, $R_f$ represents a linear partially or fully fluorinated aliphatic group or a linear partially or fully fluorinated group interrupted with one or more oxygen atoms, $X_i^+$ represents a cation having the valence i and i is 1, 2 and 3. Specific examples are described in, for example, U.S. Pat. No. 7,671,112 (Hintzer et al.). Exemplary emulsifiers include: $CF_3CF_2OCF_2CF_2OCF_2COOH$, $CHF_2(CF_2)_5COOH$, $CF_3(CF_2)_6COOH$, $CF_3O(CF_2)_3OCF(CF_3)COOH$, $CF_3CF_2CH_2OCF_2CH_2OCF_2COOH$, $CF_3O(CF_2)_3OCHFCF_2COOH$, $CF_3O(CF_2)_3OCF_2COOH$, $CF_3(CF_2)_3(CH_2CF_2)_2CF_2CF_2CF_2COOH$, $CF_3(CF_2)_2CH_2(CF_2)_2COOH$, $CF_3(CF_2)_2COOH$, $CF_3(CF_2)_2(OCF(CF_3)CF_2)OCF(CF_3)COOH$, $CF_3(CF_2)_2(OCF_2CF_2)_4OCF(CF_3)COOH$, $CF_3CF_2O(CF_2CF_2O)_3CF_2COOH$, and their salts. In one embodiment, the molecular weight of the surfactant is less than 1500, 1000, or even 500 grams/mole.

These fluorinated surfactants may be used alone or in combination as a mixture of two or more of them. The amount of the surfactant is well below the critical micelle concentration, generally within a range of from 250 to 5,000 ppm (parts per million), preferably 250 to 2000 ppm, more preferably 300 to 1000 ppm, based on the mass of water to be used.

The polymerization is usually initiated after an initial charge of monomer by adding an initiator or initiator system to the aqueous phase. For example, peroxides can be used as free radical initiators. Specific examples of peroxide initiators include, hydrogen peroxide, diacylperoxides such as diacetylperoxide, dipropionylperoxide, dibutyrylperoxide, dibenzoylperoxide, benzoylacetylperoxide, diglutaric acid peroxide and dilaurylperoxide, and further water soluble per-acids and water-soluble salts thereof such as e.g. ammonium, sodium or potassium salts. Examples of per-acids include peracetic acid. Esters of the peracid can be used as well and examples thereof include tert-butylperoxyacetate and tert-butylperoxypivalate. A further class of initiators that can be used are water soluble azo-compounds. Suitable redox systems for use as initiators include for example a combination of peroxodisulphate and hydrogen sulphite or disulphite, a combination of thiosulphate and peroxodisulphate or a combination of peroxodisulphate and hydrazine. Further initiators that can be used are ammonium- alkali- or earth alkali salts of persulfates, permanganic or manganic acid or manganic acids. The amount of initiator employed is typically between 0.03 and 2% by weight, preferably between 0.05 and 10% by weight based on the total weight of the polymerization mixture. The full amount of initiator may be added at the start of the polymerization or the initiator can be added to the polymerization in a continuous way during the polymerization. One can also add part of the initiator at the start and the remainder in one or separate additional portions during the polymerization. Accelerators such as for example water-soluble salts of iron, copper and silver may preferably also be added.

During the initiation of the polymerization reaction, the sealed reactor kettle and its contents are conveniently preheated to the reaction temperature. Polymerization temperatures are from 20° C. to 150° C., preferred from 30° C. to 110° C. and most preferred from 40° C. to 100° C. The polymerization pressure is typically between 4 and 30 bar, in particular 8 to 20 bar. The aqueous emulsion polymerization system may further comprise auxiliaries, such as buffers and complex-formers. Organic free radical initiators such as perfluoroalkyl- or perfluoroacyl-peroxide (e.g., $C_3F_7C(=O)-O-O-C(=O)C_3F_7$) can also be used, particularly when the polymerization is carried out in an inert organic solvent as known in the art.

The amount of polymer solids that can be obtained at the end of the polymerization is typically between 10% and 45% by weight, preferably between 20% and 40% by weight.

After polymerization, the resulting aqueous dispersion may be upconcentrated to increase the solid content. Non-ionic surfactants (e.g., those sold under the trade designations of "TRITON" and "GENAPOL") may be used in amounts of 2 to 10% by weight of the non-ionic surfactant to further upconcentrate the aqueous dispersion to a solid content of 40-60% as is known in the art. See for example, U.S. Pat. No. 6,833,403 (Bladel et al.) and C.A. Pat. No. 2522837 (Bladel et al.).

Alternatively, or in addition to upconcentrating the aqueous dispersion, the perfluoropolymer particles may be isolated from the aqueous dispersion by coagulation and dried. Such coagulation methods are known in the art and include chemical and physical methods, for example, using an electrolyte or inorganic salt (such as HCl, $H_2SO_4$, $HNO_3$, $H_3PO_4$, $Na_2SO_4$, $MgCl_2$, ammonium carbonate, etc.), using freeze-thaw cycles, applying high sheer, and/or applying ultrasonics.

In one embodiment, the average particle size of the resulting perfluoropolymer in an aqueous emulsion is typically at least 50, 60, 70, or even 80 nm and at most 100, 200, 300, 400, or even 500 nm (nanometers).

In one embodiment, the samples made from the perfluoropolymers of the present disclosure are optically clear, meaning that they have both a high % specular transmittance and low % haze (the ratio of diffuse transmittance to total transmittance) of the incident light in the visible spectrum (about 400 to 800 nm wavelengths). The specular transmittance can be determined by measuring the total transmittance and the diffuse transmittance and subtracting the diffuse transmittance spectrum from the total transmittance spectrum as described in the Example section below. In one embodiment, the perfluoropolymers of the present disclosure and/or articles made therefrom, have an average specular transmittance of at least 75, 80, 85, or even 90% over the entire visible light range (defined here as 400 to 800 nm) when tested by the UV-Vis method disclosed below. In another embodiment, the perfluoropolymers of the present disclosure and/or articles made therefrom, have a specular transmittance of at least 75, 80, 85, or even 90% at 500 nm when tested by the UV-Vis method disclosed below. Haze can be determined by the ratio of diffuse transmittance to total transmittance of the incident light in the visible spectrum as discusses in the UV-Vis method disclosed below. Haze can also be determined according to ASTM D1003-13, using CIE Source C. In one embodiment, the perfluoropolymers of the present disclosure and/or articles made therefrom, have a haze of less than 15, 10, or even 5%. In another embodiment, the perfluoropolymers of the present disclosure and/or articles made therefrom, have a haze of less than 15, 10, or even 5% at 500 nm.

In one embodiment, the perfluoropolymers of the present disclosure have a glass transition temperature greater than at least 10, 15, 20, 25, 30, 35, 40, or even 45° C., and at most 150, 120, 110, 100, 95, 90, or even 80° C. Although not wanting to be limited by theory, it is believed that the perfluorocycloaliphatic methyl vinyl ether monomers disclosed herein increase the glass transition temperature of the resulting perfluoropolymer. In some embodiments, the perfluoropolymer derived from the perfluorocycloaliphatic methyl vinyl ether monomer has a glass transition temperature of at least 6, 7, 8, 10, or even 12° C. higher than the glass transition temperature of the same polymer that was not derived from the perfluorocycloaliphatic methyl vinyl ether monomer.

In one embodiment, the perfluoropolymers of the present disclosure are soluble in halogenated solvents (at least 3, 5, 7, or even 10% by weight), including perfluorinated solvents such as those available under the trade designation "3M FLUORINERT ELECTRONIC LIQUID" including FC-70, FC-75, and FC-72 available from 3M Co., Maplewood, MN; highly fluorinated solvent such as those available under the trade designation "3M NOVEC ENGINEERED FLUID" such as NOVEC 7200, 7300, and 7500 available from 3M Co.; and chlorinated solvents such as those available under the trade designation "FREON" including R-22 available from The Chemours Co., Wilmington DE and "Halocarbon 0.8 Oil" available from Halocarbon Products Corp, Peachtree Corners, GA.

In one embodiment, the perfluoropolymers of the present disclosure are dissolved in a solvent in an amount of at least 0.01, 0.1, 0.5, 1, 1.5, or even 2% and at most 2.5, 3, 4, 5, 6, 8, or even 10 wt % per total weight of the solution. In one embodiment, this solution is used to coat a substrate such as a metal (stainless steel, aluminum, etc.), glass, or plastic. Exemplary solvents include the halogenated solvents as disclosed above.

In one embodiment, the $T_g$ of the perfluoropolymers of the present disclosure are at least 25, 30, 35, or even 40° C.; and at most 50, 75, 100, or even 125° C.

In one embodiment, the perfluoropolymers of the present disclosure may be used to form articles, for example by molding to form an article or coated using for example, spin coating or dip coating.

EXAMPLES

Unless otherwise noted, all parts, percentages, ratios, etc. in the examples and the rest of the specification are by weight, and all reagents used in the examples were obtained, or are available, from general chemical suppliers such as, for example, Millipore-Sigma, Saint Louis, Missouri, or may be synthesized by conventional methods.

The following abbreviations are used in this section: mL=milliliters, g=grams, wt %=percent by weight, mmHg=millimeters of mercury, NMR=nuclear magnetic resonance, mol=moles, ° C.=degrees Celsius, psi=pounds per square inch, MPa=megaPascals, nm=nanometers.
Characterization Methods The presence of a melting point and the glass transition temperatures ($T_g$) of the perfluoropolymers were determined by a differential scanning calorimetry (DSC, Q2000 by TA Instruments, New Castle, DE) under a nitrogen flow. The sample size was 5 mg±0.25 mg. A DSC thermogram was obtained from the second heat of a heat/cool/heat cycle. The first heat cycle started at −80° C. and was ramped at a rate of 10° C./min up to 350° C. The cooling cycle started at 350° C. and was cooled to −80° C. at 10° C./min. The second heat cycle started at −80° C. and was ramped at a rate of 10° C./min back up to 350° C.

The Mooney viscosity value of the perfluoropolymer was measured in a similar manner as ASTM D 1646-06 Type A by a MV2000 instrument (available from Alpha Technologies, Ohio) using large rotor (ML 1+10) at 121° C. Results are reported in Mooney units.

The specular transmittance and haze over the ultraviolet and visible (UV-Vis) wavelength for selected samples was determined as follows: Fluoropolymer discs, approximately 5 cm in diameter and approximately 28 mil (0.71 mm) thickness were made by pressing the perfluoropolymer of interest (i.e., Example 2 or 3) into a heated plate (held at 200° C.) and allowing the perfluoropolymer to heat on the plate for 3 minutes, then a heated top plate (200° C.) was pressed against the perfluoropolymer, pressing the plates together at 200 psi (1.38 MPa) for 3 minutes. Afterwards, the perfluoropolymer was removed from the plates and allowed to cool to room temperature. Two different portions of the disc were analyzed for % total hemispherical transmittance and diffuse transmittance spectra with a spectrophotometer (available under the trade designation "LAMBDA 1050 from PerkinElmer, Inc., Waltham, MA) fitted with a PELA-1002 integrating sphere accessory 6 inches (150 mm) in diameter and complies with ASTM methods E903, D1003, E308, et al. as published in "ASTM Standards on Color and Appearance Measurement", Third Edition, ASTM, 1991. Data was recorded from 850 nm to 250 nm with a scan speed of approximately 102 nm/min, with a slit width of 5 nm, UV-Vis integration of 0.56 sec/point and a 1 nm data interval the diffuse transmittance spectrum for each sample was subtracted from the total hemispherical transmittance spectra to determine the spectral transmittance. The % haze was determined by dividing the diffuse transmittance by the total transmittance. The spectra reported in the figures was taken from the average of the two analysis sites on the disc. The average specular transmittance and the average haze was taken as an unweighted average from 400 to 800 nm.

Example 1: Preparation of Formula I: $R_f$-$CF_2$—O—$CF$=$CF_2$ (Including c-$C_6F_{11}$—$CF_2$—O—$CF$=$CF_2$ (MVCc6) and its Isomers)

Methyl benzoate (4000 g, 29.4 mol) was electrochemically fluorinated in HF as described in U.S. Pat. No. 2,567,011 to give perfluorocycloaliphatic acid fluoride (for example c-$C_6F_{11}$COF and isomers thereof) comprising (3860 g, 12 mol) for a 40% yield. A 600 mL PARR 4250 benchtop reactor available from Parr Instrument Company, Moline, IL, USA, was first charged with 11 g (0.2 mol) anhydrous potassium fluoride (>99.5% purity, spray dried, available from AK Scientific), sealed and evacuated to 25 mmHg vacuum. The reactor was then charged with 514 g (1.6 mol) of perfluorocycloaliphatic acid fluoride and 50 g of diglyme available from Millipore-Sigma. The reactor was stirred and cooled to 4° C. Addition of 229 g (1.4 mol) hexafluoropropylene oxide (HFPO) available from the Chemours Company, Wilmington, DE, USA was metered into the reactor over three hours. Reactor was warmed to 25° C. and the mixture was drained. Column fractionation gave 311 g (0.6 mol) perfluorocycloaliphatic methylpropoxy acid fluoride (for example c-$C_6F_{11}CF_2OCF(CF_3)COF$ and isomers thereof) having a 156° C. boiling point for a 40% yield (based on the amount of perfluorocyclohexyl acid fluoride charged) with 356 g of recycled starting perfluorocycloaliphatic acid fluoride. Two additional HFPO coupling runs were done and combined with the first run. A 3-neck 2 L round bottom flask equipped with a mechanical stirrer, condenser and a thermocouple was charged with 168 g (1.6 mol) of $Na_2CO_3$ and 300 g glyme available from Millipore-Sigma stirred and heated to 70° C. Addition of 650 g (1.3 mol) perfluorocycloaliphatic methylpropoxy acid fluoride over an hour reacted and gave off $CO_2$. After a one hour hold, the condenser was changed over for distillation into a receiver and glyme was removed under 50 mmHg vacuum. Once the glyme was removed, the temperature was set at 105° C. and the flask was isolated. The temperature was raised to 120° C. and $CO_2$ generated from decarboxylation allowed the vacuum to go to atmospheric pressure. Formula I monomer was produced and collected in a receiver up to a final reaction temperature of 165° C. Crude product was washed with 100 g DI (deionized) water followed with 25 g $Na_2CO_3$ in 100 g DI water and a final 100 g DI water. Fluorochemical lower phase after column fractionation gave 278 g (0.7 mol) of Formula I having a boiling point of 114° C. for a 50% yield. $^{19}$F-NMR (nuclear magnetic resonance) confirmed the monomer according to Formula I.

Example 2 Preparation of Formula I: $R_f$-$CF_2$—O—CF=$CF_2$ (Including c-$C_6F_{11}$—$CF_2$—O—CF=$CF_2$ (MVCc6) and its Isomers and the 2:1 Adduct.)

Example 2 was made the same as Example 1 except with the following changes: 23 g (0.4 mol) of anhydrous potassium fluoride, 450 g (1.4 mol) of perfluorocycloaliphatic acid fluoride, 60 g of tetraglyme (instead of diglyme). 60 g of adiponitrile (Alfa Aesar) was used to charge the reactor along with the perfluorocylcoaliphatic acid fluoride and tetraglyme. Addition of 252 g (1.5 mol) HFPO was added over two hours instead of three hours. Column fractionation gave 294 g perfluorocycloaliphatic methylpropoxy acid fluoride (for example c-$C_6F_{11}CF_2OCF(CF_3)COF$ and isomers thereof) having a 156° C. boiling point for a 77% yield (based on the amount of reacted perfluorocyclohexyl acid fluoride) with 196 g of the starting perfluorocycloaliphatic acid fluoride, which was recovered and then recycled in the following HFPO coupling runs. Also isolated was 154 g (0.23 mol) of the 2:1 HPFO adduct, perfluorocycloaliphatic methoxypropoxy propanyl acid fluoride and isomers thereof. The perfluorocycloaliphatic methoxypropoxy propanyl acid fluoride and isomers thereof were decarboxylated and purified as described in Example 1 above to yield Formula I having a boiling point of 114° C. and a second cut at reduced pressure (75 mm of vacuum) to isolate 140 g of the 2:1 HFPO adduct (c-$C6F11CF2OCF(CF3)CF2OCF$=$CF2$) having a boiling point of 98-110 C. $^{19}$F-NMR (nuclear magnetic resonance) confirmed the 1;1 and 2:1 adducts.
Preparation of Emulsifying Solution An aqueous solution was prepared comprising 30 wt % of $CF_3$—O—$(CF_2)_3$—O—CFH—$CF_2$—$COONH_4$ (prepared as described in Example 11 of U.S. Pat. No. 7,671,112) spiked with 1.5 wt % of a liquid available under the trade designation 3M FLUORINERT ELECTRONIC LIQUID FC-70 from 3M Company.

Preparation of MVCc6 Solution 1
An aqueous solution of Formula I was prepared comprising 22 wt % of Formula I (from above) in the Emulsifying Solution
Preparation of MVCc6 Solution 2
An aqueous solution of Formula I was prepared comprising 60 wt % of Formula I (from above) in the Emulsifying Solution Example 3: Fluoropolymer a Preparation A 4 liter reactor was charged with 1,850 g water and was evacuated. This vacuum and pressurization was repeated three times. After removing oxygen, the reactor was heated to 72.2° C. (162° F.) and 5.2 g of potassium phosphate was added along with 48 g the Emulsifying Solution, 5.2 g ammonium persulfate and 4.26 g ammonium hydroxide. The vacuum was broken and the reactor was pressurized with perfluoropropyl vinyl ether (PPVE) to 0 psi (0 MPa). The reactor was then pressurized to 145 psi (1.0 MPa) with TFE (tetrafluoroethylene) and PPVE at a 0.88 weight ratio. The reactor was agitated at 650 rpm. As reactor pressure dropped due to monomer consumption in the polymerization reaction, TFE and PPVE at a 0.76 weight ratio was continuously fed to the reactor to maintain the pressure at 145 psi (1.0 MPa). MVCc6 Solution 1 was continuously fed at a 0.76 weight ratio to PPVE feed when 5% (25 grams) of TFE was added. After 284 minutes, the monomer feeds were discontinued and the reactor was cooled. The resulting aqueous dispersion had a solid content of 30.4 wt % and a pH of 2.4. The aqueous dispersion particle size was 189 nm.

To coagulate the aqueous dispersion, the same amount of a $MgCl_2$/DI water solution was added to the aqueous dispersion. The $MgCl_2$/DI water solution contained 1.25 wt % $MgCl_2.6H_2O$. The aqueous dispersion was agitated and coagulated. The fluoropolymer contained 76 mol % copolymerized units of TFE, 23 mol. % PPVE and 1.0 mol % Formula I by $^{19}$F-NMR. The perfluoropolymer had no discernable melting point when examined by DSC, a Tg of 12.1° C. The perfluoropolymer had a Mooney viscosity ML [1+10] @121° C. of 10.3 Mooney units. The $^{19}$F and H NMR analysis using a solvent (d3-perfluorotoluene) showed the copolymer to contain approximately 76.0 mol % TFE, 22.9 mol % PPVE, 0.49 mole % of the perfluorocyclohexyl methyl vinyl ether, 0.54 mol % of the combined perfluoro (2-methyl cyclopentyl methyl vinyl ether) and perfluoro(3-methyl cyclopentyl methyl vinyl ether) isomers, and 0.035 mol % of the combined perfluoro(2-dimethyl cyclobutyl methyl vinyl ether), perfluoro(3-dimethyl cyclobutyl methyl vinyl ether) and perfluoro(1-methyl cyclopentyl methyl vinyl ether) isomers.

Comparative Example: Fluoropolymer B Preparation

Fluoropolymer B was prepared as Fluoropolymer A except that Formula I monomer was not fed to the reactor. After 214 minutes, the monomer feeds were discontinued and the reactor was cooled. The resulting aqueous dispersion had a solid content of 34 wt % and a pH of 2.9. The aqueous dispersion particle size was 85 nm.

To coagulate, the same amount of a $MgCl_2$/DI water solution was added to the aqueous dispersion. The $MgCl_2$/DI water solution contained 1.25 wt % $MgCl_2.6H_2O$. The aqueous dispersion was agitated and coagulated. The perfluoropolymer had no discernable melting point when examined by DSC, a Tg of 4.4° C. The perfluoropolymer had a Mooney viscosity ML [1+10] @121° C. of less than 1.3 Mooney units.

Example 4: Fluoropolymer C Preparation

A 4 liter reactor was charged with 2,000 g water and was evacuated. This vacuum and pressurization was repeated three times. After removing oxygen, the reactor was heated to 57.2° C. (135° F.). To the reactor was added 28 g of Emulsifying Solution, 75 g of MVCc6 Solution 2, 4.26 g ammonium hydroxide and 5.2 g ammonium persulfate. The vacuum was broken with nitrogen and the reactor was pressurized with TFE to 0.52 MPa (75 psi). The reactor was agitated at 650 rpm. As reactor pressure dropped due to monomer consumption in the polymerization reaction, MVCc6 Solution 2 and TFE at a 1.54 weight ratio was continuously fed to the reactor to maintain the pressure at 0.52 MPa (75 psi). After 229 minutes, the monomer feeds were discontinued and the reactor was cooled. The resulting aqueous dispersion had a solid content of 19.0 wt % and a pH of 3.0. The aqueous dispersion particle size was 695 nm.

Figure 2:
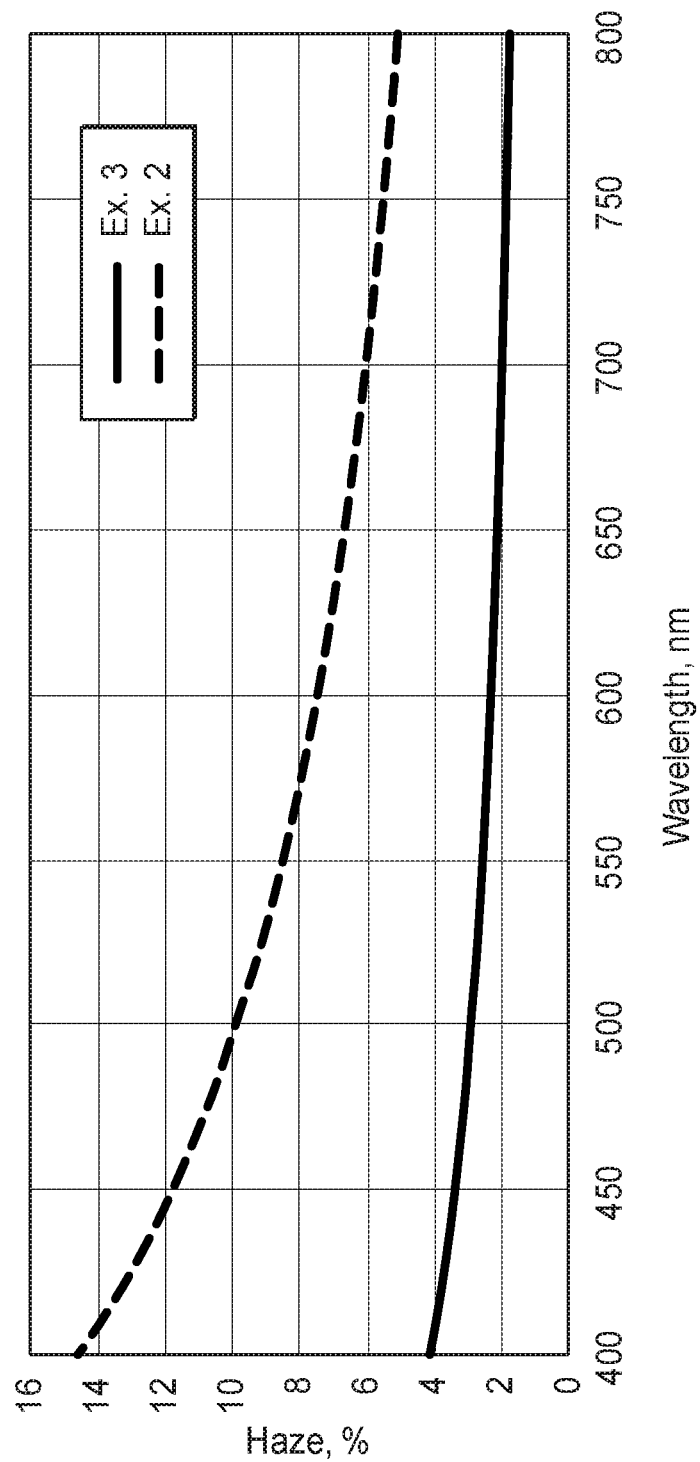
FIG. 2 is the percent haze versus wavelength for Examples 2 and 3.

The aqueous dispersion was freeze-coagulated, repeatedly washed with DI water and then dried at 130° C. Incorporation of the Formula I monomer into the perfluoropolymer was quantified using the cyclic CF resonance (−184 ppm) using Solid State $^{19}$F-NMR at 150° C. and the fluoropolymer contained 86.5 mol % copolymerized units of TFE and 13.5 mol. % Formula I. The perfluoropolymer had no discernable melting point when examined by DSC, a Tg of 40.5° C. The % specular transmittance from 400 to 800 nm is shown in FIG. 1 and the % haze from 400 to 800 nm is shown in FIG. 2. The average specular transmittance across the 400 to 800 nm range was 82.4%. The average haze across the 400 to 800 nm range was 8.2%.

Example 5: Fluoropolymer D Preparation

A 4 liter reactor was charged with 2,000 g water and was evacuated. This vacuum and pressurization was repeated three times. After removing oxygen, the reactor was heated to 57.2° C. (135° F.). To the reactor was added 28 g of Emulsifying Solution, 75 g of MVCc6 Solution 2, 4.26 g ammonium hydroxide and 5.2 g ammonium persulfate. The vacuum was broken with nitrogen and the reactor was pressurized with TFE to 0.52 MPa (75 psi). The reactor was agitated at 650 rpm. As reactor pressure dropped due to monomer consumption in the polymerization reaction, MVCc6 Solution 2 and TFE at a 1.83 weight ratio was continuously fed to the reactor to maintain the pressure at 0.52 MPa (75 psi). After 280 minutes, the monomer feeds were discontinued and the reactor was cooled. The resulting aqueous dispersion had a solid content of 20.6 wt % and a pH of 3.4. The aqueous dispersion particle size was 493 nm.

The aqueous dispersion was freeze-coagulated, repeatedly washed with DI water and then dried at 130° C. Incorporation of the Formula I monomer into the perfluoropolymer was quantified using the cyclic CF resonance (−184 ppm) using Solid State $^{19}$F-NMR at 150° C. and the fluoropolymer contained 79.5 mol % copolymerized units of TFE and 20.5 mol. % MVCc6.

The perfluoropolymer had no discernable melting point when examined by DSC and a Tg of 41.7° C. The % specular transmittance from 400 to 800 nm is shown in FIG. 1 and the % haze from 400 to 800 nm is shown in FIG. 2. The average specular transmittance across the 400 to 800 nm range was 92.2%. The average haze across the 400 to 800 nm range was 2.5%.

Foreseeable modifications and alterations of this invention will be apparent to those skilled in the art without departing from the scope and spirit of this invention. This invention should not be restricted to the embodiments that are set forth in this application for illustrative purposes. To the extent that there is any conflict or discrepancy between this specification as written and the disclosure in any document mentioned or incorporated by reference herein, this specification as written will prevail.

What is claimed is:

1. A perfluoropolymer, wherein the perfluoropolymer is derived from at least:
   (a) no more than 88 mol % tetrafluoroethylene monomer; and
   (b) a complementary amount of a monomer according to Formula I

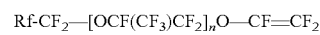
   Rf-CF$_2$—[OCF(CF$_3$)CF$_2$]$_n$O—CF=CF$_2$ wherein Rf is a perfluorinated group comprising 6 carbon atoms and 11 fluorine atoms and a cycloaliphatic group, and n is 0, 1, or 2; and
   wherein the perfluoropolymer has substantially no melting point.

2. The perfluoropolymer according to claim 1, wherein the monomer of Formula I comprises perfluoro(cyclohexyl methyl vinyl ether).

3. The perfluoropolymer according to claim 1, wherein the monomer of Formula I comprises at least one of perfluoro(cyclohexyl methyl vinyl ether), perfluoro(2-methyl cyclopentyl methyl vinyl ether), perfluoro(3-methyl cyclopentyl methyl vinyl ether), perfluoro(2-dimethyl cyclobutyl methyl vinyl ether), and perfluoro(3-dimethyl cyclobutyl methyl vinyl ether).

4. The perfluoropolymer according to claim 1, wherein the perfluoropolymer is further derived from at least one of hexafluoropropylene, chlorotrifluoroethylene, a perfluoroalkyl vinyl ether, a perfluoralkyl allyl ether, and combinations thereof.

5. The perfluoropolymer according to claim 4, wherein the perfluoropolymer is further derived from at least 10 mol % of a perfluoroalkyl vinyl ether, a perfluoroalkyl allyl ether, or combinations thereof.

6. The perfluoropolymer according to claim 1, wherein the perfluoropolymer is derived from at least 15 mol % of the perfluoro(cycloaliphatic methyl vinyl ether) monomer.

7. The perfluoropolymer according to claim 1, wherein the perfluoropolymer is further derived from a perfluorinated vinyl ether acid, a perfluorinated vinyl ether ester, a perfluorinated vinyl ether sulfonates, perfluorinated vinyl ether sulfonyl fluoride, perfluorinated vinyl ether phosphates, or combinations thereof.

8. The perfluoropolymer according to claim 1, wherein the glass transition temperature of the perfluoropolymer is above room temperature.

9. The perfluoropolymer according to claim 1, wherein the perfluoropolymer is optically clear.

10. The perfluoropolymer according to claim 1, wherein the perfluoropolymer has an average specular transmittance of at least 75% over the entire visible range.

11. The perfluoropolymer according to claim 1, wherein the perfluoropolymer has an average haze of less than 15% over the entire visible range.

12. A fluoropolymer comprising at least one interpolymerized monomeric unit of

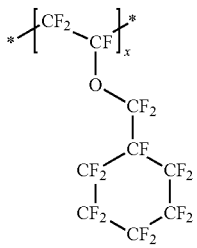
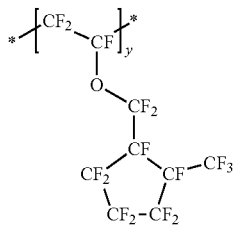
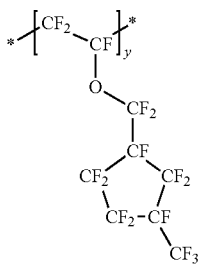
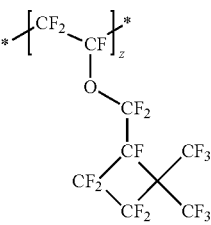
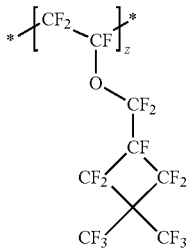
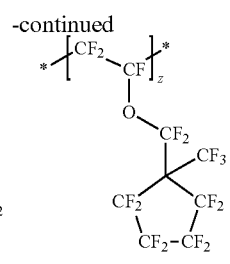

and combinations thereof wherein x, y, and z are independently at least 2 repeat units, and wherein the polymer has substantially no melting point.

13. The fluoropolymer of claim 12, wherein the polymer has a glass transition temperature greater than room temperature.

14. The fluoropolymer of claim 12, wherein the fluoropolymer is optically clear.

15. The fluoropolymer of claim 12, wherein the fluoropolymer further comprises interpolymerized units derived from tetrafluoroethylene.

16. The fluoropolymer of claim 15, wherein the fluoropolymer comprises no more than 88 mole % of interpolymerized units derived from tetrafluoroethylene.

17. The fluoropolymer of claim 12, wherein the fluoropolymer further comprises interpolymerized units derived from a perfluorinated vinyl ether acid, a perfluorinated vinyl ether ester, or combinations thereof.

18. A composition comprising the fluoropolymer of claim 12.

19. The composition of claim 18, wherein the composition is a coating.

* * * * *